United States Patent [19]

Chen

[11] Patent Number: 5,328,475
[45] Date of Patent: Jul. 12, 1994

[54] SIMPLIFIED SAFETY SYRINGE WITH RETRACTABLE SELF-BIASED NEEDLE

[76] Inventor: Long-Hsiung Chen, c/o Hung Hsing Patent Service Center, P.O. Box 55-1670, Taipei (104), Taiwan

[21] Appl. No.: 167,012
[22] Filed: Dec. 16, 1993
[51] Int. Cl.$^5$ ............................................ A61M 5/32
[52] U.S. Cl. ................................ 604/110; 604/195
[58] Field of Search ................ 604/110, 195, 192

[56] References Cited

U.S. PATENT DOCUMENTS

| 4,955,870 | 9/1990 | Reddersheim et al. | 604/198 |
| 4,986,813 | 1/1991 | Blake, III et al. | 604/110 |
| 5,171,300 | 12/1992 | Blake, III et al. | 604/195 |
| 5,205,826 | 4/1993 | Chen | 604/195 |
| 5,232,458 | 8/1993 | Chen | 604/195 |
| 5,242,402 | 9/1993 | Chen | 604/195 |
| 5,273,539 | 12/1993 | Chen | 604/110 |

Primary Examiner—Paul J. Hirsch

[57] ABSTRACT

A safety syringe includes: a hollow needle normally held in a front portion of a syringe, a plunger slidably held in the syringe for injection use, a coupling member retained in the plunger engageable with at least a biasing socket recessed in a rear needle portion of the hollow needle with the biasing socket generally formed as a conical shape having a longitudinal conical axis inclined from a needle axis of the needle when normally fixed in the syringe with the needle axis aligned with a syringe axis longitudinally formed in a center line of the syringe, whereby upon retraction of the plunger and the needle coupled to the plunger, with the biasing socket of the needle forcibly coupled with the coupling member, into a bore portion in the syringe, the needle will be automatically inclined as the biasing socket of the needle is restored by the coupling member retained in the plunger to prevent an outward protruding of the retracted needle from the syringe for preventing its pricking to the others.

5 Claims, 3 Drawing Sheets

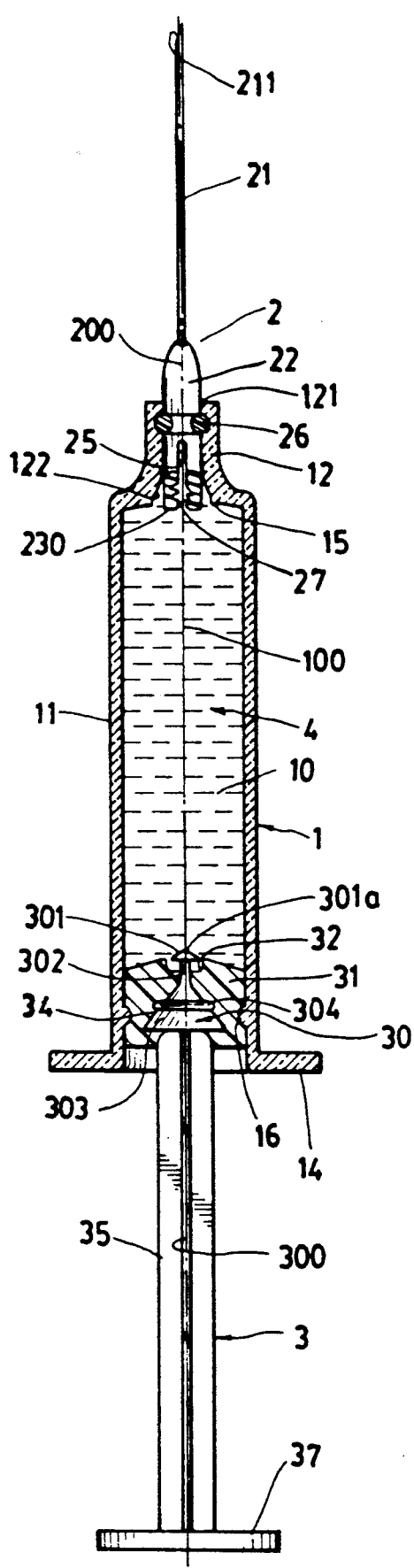
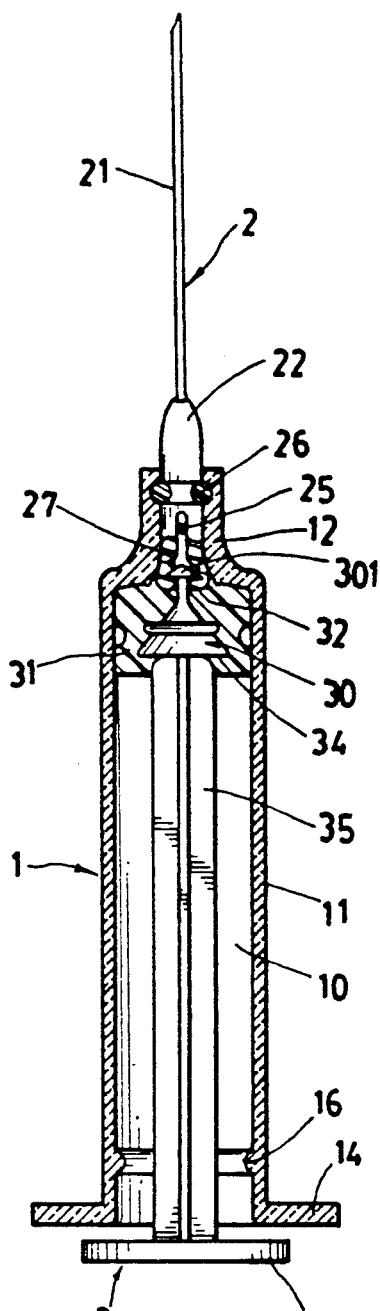
FIG. 1
FIG. 2

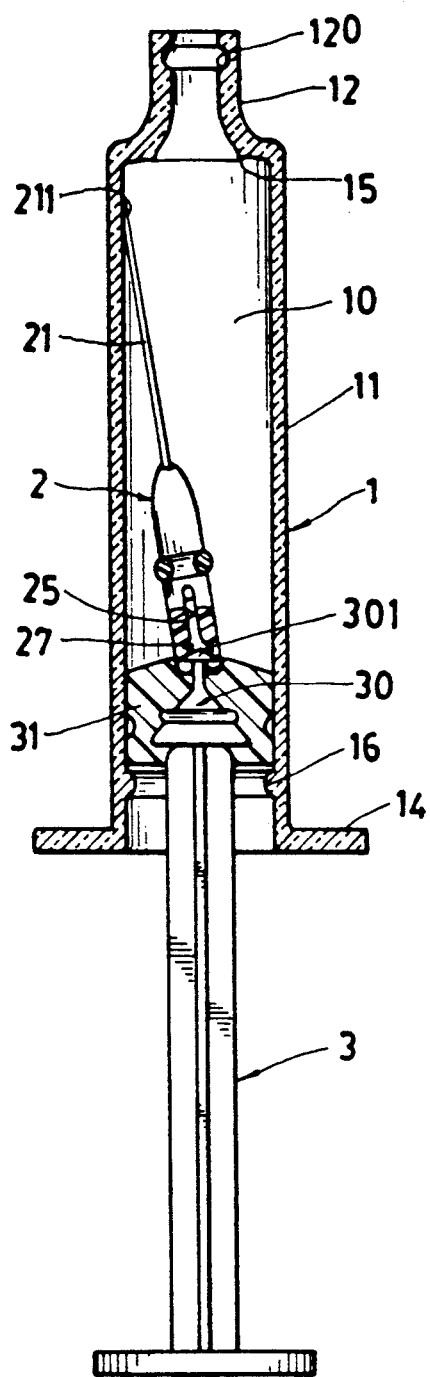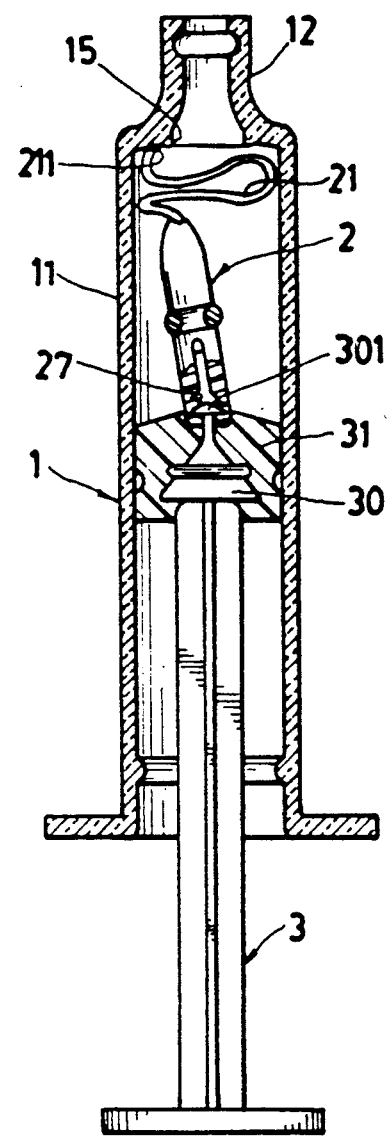
FIG.3
FIG.4

SIMPLIFIED SAFETY SYRINGE WITH RETRACTABLE SELF-BIASED NEEDLE

BACKGROUND OF THE INVENTION

U.S. Pat. No. 5,232,458 entitled "Safety Syringe with Retractable Self-biased Needle" issued to the same inventor of this application disclosed a needle secured in a plug 13 embedded in a front portion of the syringe having a needle head portion formed on a rear portion of the needle and a plunger slidably held in the syringe having a biasing socket recessed in a front portion of the plunger engageable with the needle head portion for biasing the needle obliquely within the syringe when retracting the plunger and the needle into the syringe, thereby preventing an outward protruding of the retracted needle for preventing its injury to the surroundings.

However, the plug 13 should be provided in a front portion of the syringe for holding the needle 2 in the plug 13 to be normally positioned at a front portion of the syringe 1 for injection use.

In order to save material cost and enhance assembly convenience of such a safety syringe, the plug 13 is expected to be eliminated or omitted, and the needle 2 would then be directly secured at a front portion of the syringe 1 for simplifying its production and decreasing its cost.

SUMMARY OF THE INVENTION

The object of the present invention is to provide a safety syringe including: a hollow needle normally held in a front portion of a syringe, a plunger slidably held in the syringe for injection use, a coupling member retained in the plunger engageable with at least a biasing socket recessed in a rear needle portion of the hollow needle with the biasing socket generally formed as a conical shape having a longitudinal conical axis inclined from a needle axis of the needle when normally fixed in the syringe with the needle axis aligned with a syringe axis longitudinally formed in a center line of the syringe, whereby upon pushing of the plunger to the needle by forcibly inserting the coupling member into the biasing socket when finishing the injection, the biasing socket will be forcibly coupled with the coupling member, and upon retraction of the plunger and the needle into a bore portion in the syringe, the needle will be automatically inclined when the needle is restored by the coupling member in the plunger by smoothly engaging the coupling member with the biasing socket to prevent an outward protruding of the retracted needle from the syringe for preventing its pricking to the others.

BRIEF DESCRIPTION OF THE DRAWINGS

FIG. 1 is an illustration showing the present invention ready for injection use.

FIG. 2 shows coupling of the plunger with the needle when finishing a medical injection.

FIG. 3 shows retraction of needle into the syringe of the present invention.

FIG. 4 shows a bent needle in the syringe in accordance with the present invention.

DETAILED DESCRIPTION

Figure 6:
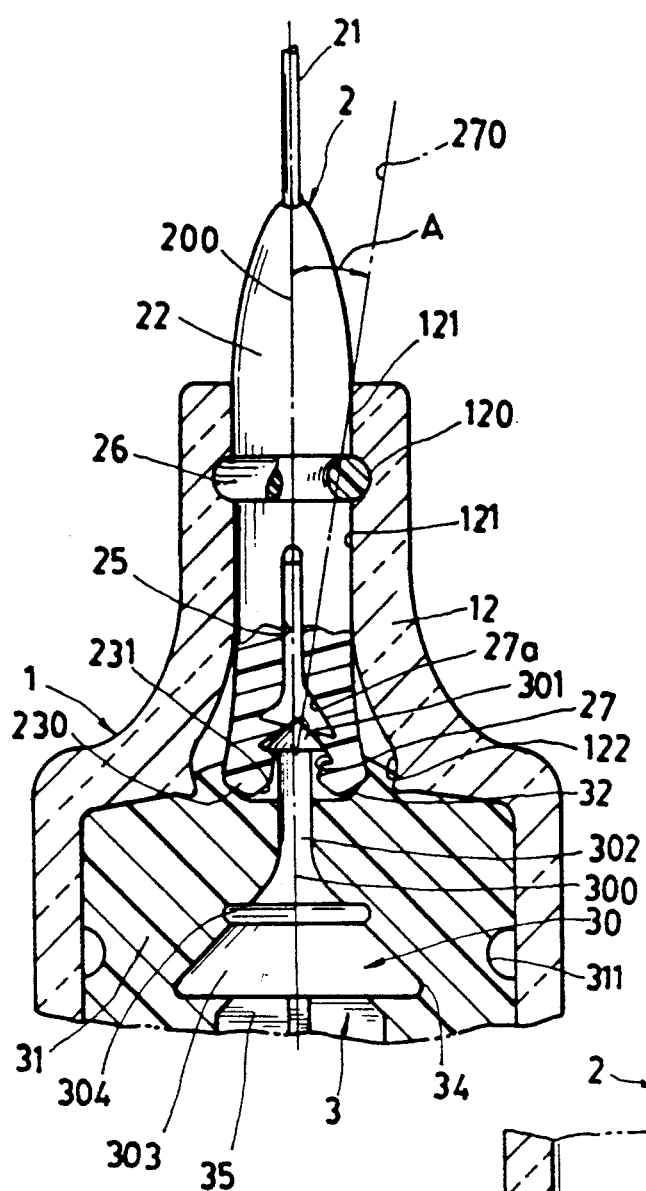
FIG. 6 shows a coupling member coupled with a rear needle portion in accordance with the present invention.
Figure 5:
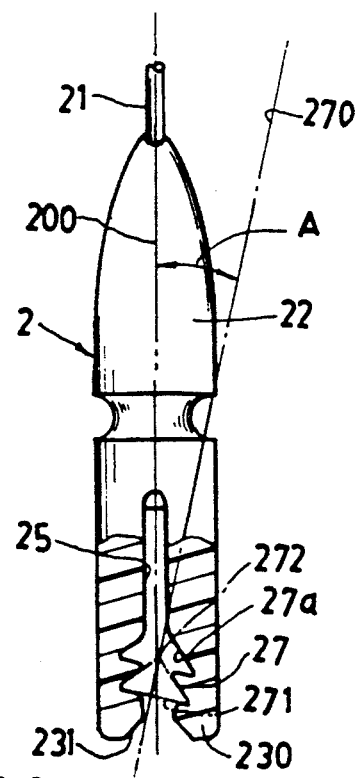
FIG. 5 is an illustration showing the needle of the present invention.

As shown in the drawing figures, the present invention comprises: a syringe means 1, a needle device 2, and a plunger means 3.

The syringe means 1 includes: a syringe cylinder 11 having a hollow bore portion 10 defined in the syringe cylinder 11 for filling liquid medicine 4 in the cylinder 11 and a syringe axis 100 longitudinally existing in a central portion of the syringe cylinder 11, a sleeve portion 12 formed on a front portion of the syringe cylinder 11 contracted forwardly from the cylinder 11 having a central opening 121 formed through the sleeve portion 12, and a diverging port 122 formed in a rear portion of the sleeve portion 12 adjacent to the syringe cylinder 11, a ring groove 120 annularly recessed in a front portion of the sleeve portion 12, a syringe handle 14 formed on a rear end portion of the cylinder 11, a blocking ring 15 annularly formed at a rear end portion of the sleeve portion 12 between the central opening 121 of the sleeve portion 12 and the bore portion 10 of the syringe cylinder 11, and an annular extension 16 annularly formed on a rear portion of the cylinder 11.

The needle device 2 includes: a needle portion 21 having a needle tip 211 formed at a front end of the needle portion 21, a shank portion 22 connected with the needle portion 21 having an annular packing ring 26 circumferentially disposed around the shank portion 22 to be engageably held in the ring groove 120 in the sleeve portion 12, a bifurcated slot 25 longitudinally formed in a rear portion of the shank portion 22 and recessed forwardly from a rear needle end portion 230, at least a biasing socket 27 generally conical shaped formed in a rear portion of the shank portion 22 and communicating with a guiding port 231 recessed forwardly from the rear needle end portion 230, and a needle axis 200 longitudinally existing in a central portion of the needle device 2, with the shank portion 22 and the rear needle end portion 230 made of resilient plastic materials.

The biasing socket 27 may be formed with plural sockets, such as two sockets 27, 27a, juxtapositionally recessed in the rear needle portion of the needle device 2, which are not limited in this invention.

The needle axis 200 will be aligned with the syringe axis 100 when the needle device 2 is normally secured on a sleeve portion 12 of the syringe means 1 for injection purpose.

Each biasing socket 27 generally conical shaped includes: a conical bottom 271, a conical apex 272 tapered forwardly from the conical bottom 271, and a longitudinal conical axis 270 aligned with the conical apex 272 to be perpendicular to the conical bottom 271 and to be inclinedly deviated from the needle axis 200 of the needle device 2 to define an acute angle A between the needle axis 200 and the longitudinal conical axis 270 of the biasing socket 27. The biasing socket 27 is snugly engageable with an arrowhead portion 301 of the plunger means 3 for obliquely biasing the needle device 2 when coupled to the plunger means 3 and retracted in the syringe cylinder 11 after finishing an injection.

The plunger means 3 includes: a plunger 31 slidably held in the syringe cylinder 11 of the syringe means 3, a coupling member 30 retained in a conical recess 34 in the plunger 31 having the arrowhead portion 301 formed on a front end of the coupling member 30 operatively insertable in a biasing socket 27 formed in the needle device 2, a holding socket 32 concentrically disposed around the arrowhead portion 301 for operatively coupling a rear needle end portion 230 when bifurcated by the arrowhead portion 301 inserted into the biasing socket 27, with the rear needle end portion 230 confined within a diverging port 122 formed in a rear portion of a sleeve portion 12 of the syringe means 1, a plunger rod 35 having a plunger handle 37 protruding rearwardly from the plunger 31 for pushing operation of the plunger 31 with the plunger 31 formed with an annular recess 311 in the plunger 31 to be engaged with an annular extension 16 formed in a rear portion of the syringe cylinder 11 for restricting a rear movement of the plunger 31, and a plunger axis 300 longitudinally defined in a central portion of the syringe means 3 normally aligned with a needle axis 200 of the needle device 2, and aligned with the syringe axis 100 of the syringe means 1.

The coupling member 30 includes: the arrowhead portion 301 being conical shaped and engageable with a conical shaped biasing socket 27 of the needle device 2 having an apex 301a of the arrowhead portion 301 aligned with the plunger axis 300, the needle axis 200 and the syringe axis 100 as shown in FIG. 1 ready for a normal medical injection, a neck portion 302 connected with the arrowhead portion 301, and a conical base portion 303 having an annular protrusion 304 circumferentially formed on a conical surface of the base portion 303 for well sealable embedding of the conical base portion 303 in the conical recess 34 in the plunger 31, with the conical base portion 303 secured to a plunger rod 35 of the plunger means 3.

When using the present invention for injection use as shown in FIG. 1, the plunger 31 may be pushed forwardly to boost the medicine 4 in the cylinder 11 through the needle device 2 to a patient's body.

The arrowhead portion 301 of the coupling member 30 will then be forcibly inserted into the biasing socket 27 of the needle device 2 to squeeze, and expansively bifurcate the rear needle portion 230 of the needle device 2 to store a resilient potential energy of the bifucated rear needle portion, thereby operatively coupling the coupling member 30 with the needle device 2 as shown in FIGS. 2, 6.

Figure 7:
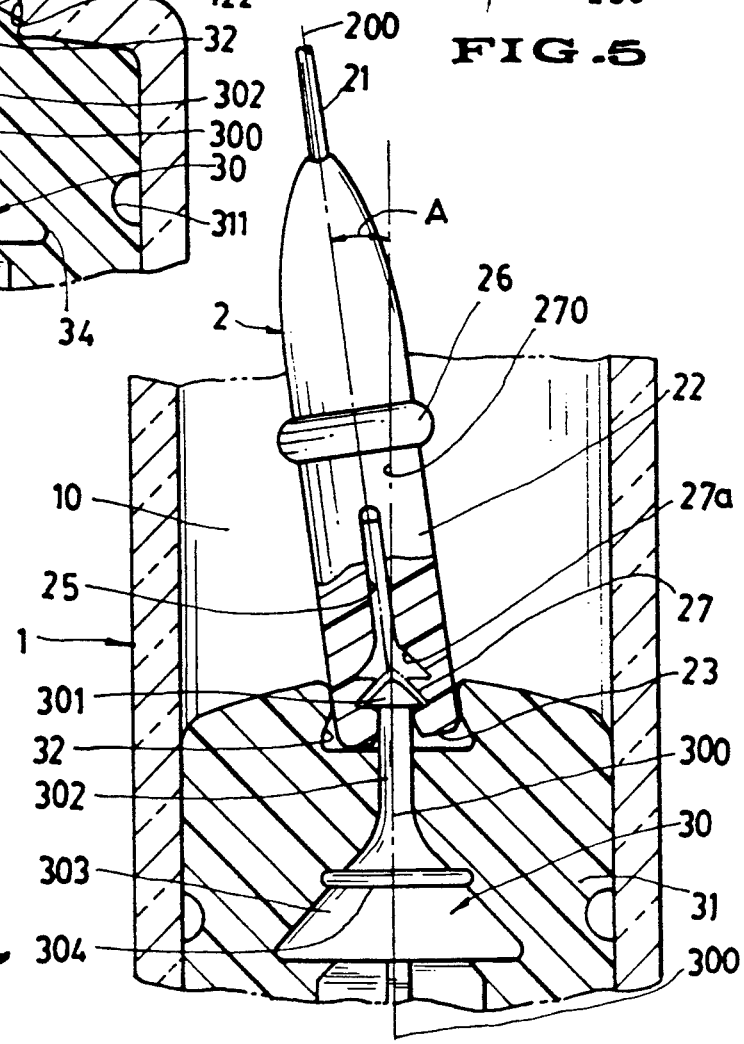
FIG. 7 shows an inclined needle when retracted in the syringe of the present invention.

After retracting the plunger 31 and the coupled needle device 2 into the bore portion 10 of the syringe cylinder 11 as shown in FIG. 3, the biasing socket 27 of the needle device 2 will be restored to be snugly engaged with the arrowhead portion 301 of the coupling member 30 of the plunger means 3 by releasing a resilient force accumulated on the rear needle portion 230 when forcibly coupling the arrowhead portion 301 with the biasing socket 27 as shown in FIGS. 2 and 6, thereby automatically obliquely biasing the needle device 2 coupled on the plunger 31 as shown in FIGS. 7 and 3. After re-protruding the needle device 2 outwardly, the needle tip 211 will be retarded against the blocking ring 15 formed in a front portion of the cylinder 11, thereby bending the needle 2 and obstructing its outward protrusion and preventing its injury or contamination to the surroundings.

The present invention is superior to the earlier invention, U.S. Pat. No. 5,232,458, also issued to the same inventor of this application since the plug 13 of the earlier invention has been eliminated, thereby saving cost and enhancing installation convenience.

Meanwhile, the needle device 2 can be conveniently replaced with diversified sizes (number of needles) directly by withdrawing a used needle 2 from the sleeve portion 12 and then by re-inserting a new needle into the sleeve portion 12 through a front opening end of the sleeve portion 12.

I claim:
1. A safety syringe comprising:
a syringe means including a syringe cylinder having a hollow bore portion for filling liquid medicine therein, and a sleeve portion formed on a front portion of said syringe means having a central opening formed through the sleeve portion, a syringe axis longitudinally defined in a central portion of said syringe means;
a needle device including a hollow needle portion fixed on a shank portion held in said sleeve portion of said syringe means having at least a biasing socket generally conical shaped recessed in a rear needle portion of said needle device having a longitudinal conical axis obliquely deviating an acute angle from a needle axis which is longitudinally defined in a central portion of said needle device and is aligned with the syringe axis of said syringe; and
a plunger means including a plunger slidably held in said syringe cylinder for boosting liquid medicine in said cylinder for injection through said needle device, and a coupling member embedded in said plunger having an arrow head portion formed at a front end of said coupling member operatively forcibly inserted in said biasing socket to couple the arrowhead portion with the needle device to store a resilient restoring energy of the rear needle portion of said needle device after finishing an injection, and upon retraction of the plunger and the needle device coupled to said plunger into said syringe cylinder, said needle device will be automatically restored and obliquely biased to prevent outwardly re-protruding of said needle device from said syringe means.

2. A safety syringe according to claim 1, wherein said needle device (2) includes: a needle portion (21) having a needle tip (211) formed at a front end of the needle portion (21), a shank portion (22) connected with the needle portion (21) having an annular packing ring (26) circumferentially disposed around the shank portion (22) to be engageably held in the ring groove (120) in the sleeve portion (12), a bifurcated slot (25) longitudinally formed in a rear portion of the shank portion (22) and recessed forwardly from a rear needle end portion (230), at least a biasing socket (27) generally conical shaped formed in a rear portion of the shank portion (22) and communicating with a guiding port (231) recessed forwardly from the rear needle end portion (230), and a needle axis (200) longitudinally defined in a central portion of the needle device (2), with the shank portion (22) and the rear needle end portion (230) made of resilient plastic materials.

3. A safety syringe according to claim 2, wherein each said biasing socket (27) generally conical shaped includes: a conical bottom (271), a conical apex (272) tapered forwardly from the conical bottom (271), and a longitudinal conical axis (270) aligned with the conical apex (272) to be perpendicular to the conical bottom (271) and to be inclinedly deviated from the needle axis (200) of the needle device (2) to define an acute angle A between the needle axis (200) and the longitudinal conical axis (270) of the biasing socket (27), said biasing socket (27) snugly engageable with an arrowhead portion (301) of the plunger means (3) for obliquely biasing the needle device (2) when coupled to the plunger means (3) and retracted in the syringe cylinder (11) after finishing an injection.

4. A safety syringe according to claim 3, wherein said plunger means (3) includes: a plunger (31) slidably held in the syringe cylinder (11) of the syringe means (3), a coupling member (30) retained in a conical recess (34) in the plunger (31) having the arrowhead portion (301) formed on a front end of the coupling member (30) operatively insertable in a biasing socket (27) formed in the needle device (2), a holding socket (32) concentrically disposed around the arrowhead portion (301) for operatively coupling a rear needle end portion (230) when bifurcated by the arrowhead portion (301) inserted into the biasing socket (27), with the rear needle end portion (230) confined within a diverging port (122) formed in a rear portion of a sleeve portion (12) of the syringe means (1), a plunger rod (35) having a plunger handle (37) protruding rearwardly from the plunger (31) for pushing operation of the plunger (31) with the plunger (31) formed with an annular recess (311) in the plunger (31) to be engaged with an annular extension (16) formed on a rear portion of the syringe cylinder (11) for restricting a rear movement of the plunger (31), and a plunger axis (300) longitudinally defined in a central portion of the syringe means (3) normally aligned with a needle axis (200) of the needle device (2), and aligned with the syringe axis (100) of the syringe means (1).

5. A safety syringe according to claim 4, wherein said coupling member (30) includes: the arrowhead portion (301) being conical shaped and engageable with a conical shaped biasing socket (27) of the needle device (2) having an apex of said arrowhead portion (301a) aligned with the plunger axis (300), the needle axis (200) and the syringe axis (100) ready for a normal medical injection, a neck portion (302) connected with the arrowhead portion (301), and a conical base portion (303) having an annular protrusion (304) circumferentially formed on a conical surface of the base portion (303) for well sealable embedding of the conical base portion (303) in the conical recess (34) in the plunger (31), with the conical base portion (303) secured to a plunger rod (35) of the plunger means (3).

* * * * *